(12) United States Patent
Porubcan

(10) Patent No.: US 8,066,986 B2
(45) Date of Patent: Nov. 29, 2011

(54) FORMULATIONS INCLUDING DIGESTIVE ENZYMES AND POLYSORBATE SURFACTANTS THAT ENHANCE THE COLONIZATION OF ADMINISTERED PROBIOTICS MICROOGANISMS

(75) Inventor: Randolph S. Porubcan, Victoria, MN (US)

(73) Assignee: Master Supplements, Inc., Victoria, MN (US)

( * ) Notice: Subject to any disclaimer, the term of this patent is extended or adjusted under 35 U.S.C. 154(b) by 863 days.

(21) Appl. No.: 12/022,380

(22) Filed: Jan. 30, 2008

(65) Prior Publication Data

US 2008/0187525 A1    Aug. 7, 2008

Related U.S. Application Data

(60) Provisional application No. 60/887,628, filed on Feb. 1, 2007.

(51) Int. Cl.
| | |
|---|---|
| *A61K 33/00* | (2006.01) |
| *A61K 33/06* | (2006.01) |
| *A61K 38/43* | (2006.01) |
| *A01N 59/00* | (2006.01) |
| *A01N 59/06* | (2006.01) |
| *A01N 63/00* | (2006.01) |
| *C12N 1/12* | (2006.01) |
| *C12N 1/20* | (2006.01) |
| *C12N 9/00* | (2006.01) |
| *C12P 1/04* | (2006.01) |

(52) U.S. Cl. .................. 424/93.3; 424/93.45; 424/94.1; 424/600; 424/682; 435/170; 435/183; 435/252.1; 435/822; 435/853; 435/854; 435/855; 435/856; 435/857

(58) Field of Classification Search ......................... None
See application file for complete search history.

(56) References Cited

U.S. PATENT DOCUMENTS

| | | | | |
|---|---|---|---|---|
| 6,013,255 | A * | 1/2000 | Edens et al. .................. 424/94.1 |
| 2003/0054499 | A1 * | 3/2003 | Han et al. ......................... 435/97 |
| 2005/0084500 | A1 * | 4/2005 | Molly et al. .............. 424/195.15 |
| 2005/0106132 | A1 * | 5/2005 | Porubcan ................... 424/93.45 |
| 2006/0251635 | A1 * | 11/2006 | Glenn et al. ................ 424/93.45 |

* cited by examiner

*Primary Examiner* — Debbie K Ware
(74) *Attorney, Agent, or Firm* — Eric P. Mirabel

(57) ABSTRACT

Disclosed are formulations for enhancing the in vivo colonization of probiotic microorganisms that include digestive enzymes and probiotic microorganisms, and polysorbate surfactants. The enzymes include lactogenic enzyme formulations that promote growth of *Lactobacillus* probiotics, bifidogenic enzyme formulations that promote growth of *Bifidobacterium* probiotics and combination formulations that benefit both types of probiotics. It has been discovered that certain polysorbate surfactants, including polysorbate-60 and polysorbate-80, further promote probiotic microorganism growth, when used with the enzyme formulations. The formulations are preferably compounded as dry powders, to avoid water reaction with the enzymes in blended formulations. Such formulations can be contained in capsules, tablets, packets or bottles and administered orally, either sequentially or in one combined formulation.

12 Claims, No Drawings

FORMULATIONS INCLUDING DIGESTIVE ENZYMES AND POLYSORBATE SURFACTANTS THAT ENHANCE THE COLONIZATION OF ADMINISTERED PROBIOTICS MICROOGANISMS

RELATED APPLICATIONS

This application claims priority to U.S. Provisional Application Ser. No. 60/887,628, filed Feb. 1, 2007, priority to which is hereby claimed.

FIELD OF THE INVENTION

The invention relates to formulations for enhancing colonization in vivo of administered probiotic bacteria.

BACKGROUND

Dietary supplements containing viable probiotic bacteria are increasing in popularity in the marketplace as their health benefits become recognized. Reported benefits range from alleviating constipation and diarrhea to reducing various intestinal infections such as those caused by rotaviruses, pathogenic *E. coli* and *Helicobacter pylori* as discussed in U.S. Pat. Nos. 7,090,840 and 7,029,669. Beneficial species of *Lactobacillus* and bifidobacteria are among the widely recognized probiotics, and strains of these bacteria that are capable of colonizing the intestinal tract are advantageous (see U.S. Pat. Nos. 7,150,986 and 6,887,465).

Colonization may involve physical attachment to epithelial cell surfaces such as those of the microvilli in the ileum section of the small intestine, or simple domination of the contents of the cecum, or adherence within the mucin layers of the colon. There is much to learn about how probiotics colonize the mammalian intestinal tract but it has been established that when colonization occurs, more probiotic microorganisms appear in the feces and this correlates with more probiotic microorganisms in both the proximal and distal sections of the intestinal tract. See Muralidhara et al, 1997, Journal of Food Protection Vol. 40, No. 5, Pages 288-295. Young pigs were used to demonstrate the relationship between colonization and fecal probiotic counts in Muralidhara's work; the porcine intestinal tract is very similar in physiology to the human intestinal tract and similar studies with young pigs are presented in examples of the present invention to demonstrate its effectiveness.

Colonization that results in the competitive exclusion of pathogenic microorganisms is particularly beneficial and can occur when probiotics occupy most of the intestinal attachment sites and are encouraged to produce lactic acid and other antimicrobial compounds. Effective intestinal colonization by probiotics depends on the availability of proper microbial nutrition that must be provided by the diet. See Gibson et al 1995, Gastroenterology 106: 975-982; Christl et al, 1992, Gut 33: 1234-1238 and Reid et al, 1990, Clin. Microbiol. Rev. 3: 335-344. However, normal diets do not provide nutrients that necessarily benefit probiotics so there is a need to fortify the diet with such nutrients. Prebiotics are one class of microbial nutrients that are currently popular in the marketplace. They are typically certain oligosaccharides that are not digested in the small intestine but serve as nutrients for select probiotic bacterial genera, e.g., bifidobacteria, when they arrive in the colon. An article titled "Prebiotics Enhance Gut Health" by Laura Brandt is available online at the nutrasolutions website; another titled "Prebiotics: A More Reliable Way to Increase Gut-Friendly Bacteria" by Dr. James Meschino is available at the chiroweb website, in the archival section. Today, a variety of functional foods are fortified with prebiotics such as fructooligosaccharides (FOS) and inulin, in an effort to provide probiotic stimulation in vivo. This practice adds cost to the foods being fortified and is not very effective in stimulating *Lactobacillus* probiotics. Thus, there is a need for reducing the cost of prebiotics while providing for both *Lactobacillus* and *Bifidobacterium* stimulation.

Although enzymes have been used to generate prebiotics under laboratory conditions followed by subsequent feeding of the preformed prebiotics to achieve probiotic stimulation (see U.S. Pat. Nos. 6,791,015 and 6,730,502), no one has suggested using enzymes to generate these effects in vivo. U.S. Pat. No. 5,817,350 discloses the use of the prebiotic enzymes cellulose, amylase and hemicellulase, for use as dietary supplements, but not use of these enzymes to stimulate administered probiotics, or enhancement of their prebiotic effect by addition of polysorbate compounds. U.S. patent application 20010031276 discloses the use of polysorbate compounds as feed additives for ruminant animals but does not relate to their use in combination with prebiotics and probiotics, or their use in non-ruminant animals.

If polysorbate surfactants are combined with enzymes, water activity (Aw) becomes important. High levels of Aw, e.g., Aw>0.04, can significantly destabilize the shelf life of certain enzymes. Polysorbates are viscous, sticky, non-aqueous liquids that are not available in dry form. Before incorporation into enzyme formulations, polysorbates must be rendered into dry powders and the Aw of any formulation containing them should be below 0.04.

"Internal Probiotic Culture" or IPC, as used herein, is the totality of viable probiotic microorganisms present in the intestinal tract at any given time: i.e., the sum of probiotic microorganisms adhering to intestinal epithelial cells, mucous and mucin layers, ingested food and waste material. It is desirable to enhance the IPC of humans and mammals. IPC can be estimated from the total viable *Lactobacillus* and/or Bifidobacteria counts (colony forming units) present in fresh fecal matter.

SUMMARY

Described herein are formulations of probiotics, enzymes to enhance or stimulate the growth of probiotics and food grade polysorbate surfactants that enhance the growth-stimulating effect of the enzymes. The enzymes catalyze generation of microbial nutrients in vivo such as cobiotics and prebiotics (cobiotics are nutrients utilized by both the host and the probiotics; prebiotics are substances utilized only by probiotics).

It was discovered that certain digestive enzymes have the ability, upon reacting with food, to produce nutrient substances in vivo that are stimulatory to some probiotics, including the *Lactobacillus* and *Bifidobacterium* species. Enzymes such as proteases and amylases (that produce free amino acids and simple monosaccharides) primarily stimulate *Lactobacillus* probiotics and are referred to herein as lactogenic enzymes. Enzymes such as cellulase and hemicellulase (that release prebiotic oligosaccharides or crack larger polysaccharides into oligosaccharides) primarily stimulate Bifidobacteria probiotics and are referred to herein as bifidogenic enzymes.

In one administration embodiment, the probiotics are administered in advance of the enzymes, or in advance of both enzymes and polysorbates, by 2-72 hours to allow an internal probiotic culture (IPC) to develop in the intestinal tract. The IPC is enhanced, as demonstrated in vitro and in vivo in the examples provided below. Subsequent to the initial establishment of the IPC, which begins on day one of an administration program with the first dose of a probiotic formulation, e.g., with a dose of at least about 5 billion colony forming units (CFU), the probiotic, enzyme or enzyme plus polysorbate formulations are thereafter administered daily, or less frequently.

Probiotic administration will preferably precede the enzyme or enzyme plus polysorbate administration by about 4-12 hours. This delay allows the probiotics time to become established on the intestinal surfaces, and/or as an IPC, prior to action by the enzymes or their reaction products. This delay also limits direct interaction of the probiotics with the enzymes.

The result of administration of probiotics, enzymes and polysorbates as described herein is a substantial increase in the Internal Probiotic Culture (IPC).

DETAILED DESCRIPTION

Lactogenic enzymes are those that release cobiotics (free amino acids, short chain peptides, and monosaccharide sugars) from ingested food. They stimulate the colonization and/or strength of the Internal Probiotic Culture (IPC) of *Lactobacillus* probiotics when used as described herein. Bifidogenic enzymes are those that either release existing prebiotic oligosaccharides from food or enzymatically crack larger food borne polysaccharides into oligosaccharides that have prebiotic activity. They stimulate the colonization or IPC of bifidobacteria probiotics when used s described herein. Polysorbates such as Tween-60 and Tween-80 have been found to stimulate the effects of lactogenic and bifidogenic enzymes.

The various formulations herein can be packaged in capsules, tablets, packets or bottles and then into kits that provide all the necessary components for probiotic stimulation in a consumer ready format. Although the various ingredients could be utilized as liquids, dry formulations are preferred.
Lactogenic Enzyme Formulations (LEF)

The lactogenic enzyme formulations of this invention contain protease and carbohydrase digestive enzymes. Exemplary lactogenic enzymes include the following proteases: papain from *Carica papaya* (800 TU/mg), bromelain from *Ananas comosus* (2,000 GDU/g), fungal protease from *Aspergillus oryzae* (400,000 HU/g), acid protease from *A. oryzae* (500,000 HUT/g), bacterial protease from *Bacillus subtilis* (2,000,000 PC/g), and fungal peptidase from *Aspergillus oryzae* (500 LAP/g); and the following carbohydrases: alpha-amylase from *A. oryzae* (100,000 SKB/g), glucoamylase from *A. niger* (1,000 AG/g), lactase from *A. oryzae* (100,000 ALU/g), and invertase from *Saccharomyces cerevisiae* (200,000 Summer U/g). Activity units are shown in parenthesis for the stock enzyme concentrates that are obtained from a commercial source (and are defined below in Table I), but are not necessarily the activity for the final formulations. All enzymes are dry powders obtained from Bio-Cat, Inc., Troy, Va.

Many other enzymes such as pancreatin (a mixture of enzymes), trypsin, chymotrypsin and pepsin that are derived from animal tissue can be used to achieve some of the benefits of the present invention but may not exhibit significant enzymatic activity deep in the intestinal tract as effectively as the fungal enzymes indicated above. New to the market are enzymes such as nattokinase and serrapeptase that can also be used (though they were not approved for use in foods prior to October 1994).

Specific formulations are made by combining one or more lactogenic enzyme with MCC (microcrystalline cellulose available as Avicel PH112 from FMC, Philadelphia, Pa.) used as an inert carrier to standardize enzyme strength (activity units). MCC may comprise 10-80% of the formulation depending on the quantity of other ingredients used. In addition, food-grade silica such as Syloid 63 FP (W.R. Grace, Columbia, Md.) can be added at 2% by weight to improve dry flow characteristics and reduce water activity (Aw). Optionally, up to 2% by weight pharmaceutical grade magnesium stearate is added if the formulation is to be filled into capsules or tableted. All ingredients may be blended in a Paterson-Kelly type twin-cone blender to achieve a uniform mixture, typically requiring 10-15 minutes mixing at 50 rpm. For purposes of reducing Aw and enhancing shelf-life, all operations should be conducted in a dry, humidity controlled facility having a relative humidity of 20-40%. The final formulation can be filled directly into hard capsules made of gelatin, cellulose, HPMC or any suitable capsule material, or into hermetically sealed packages or bottles.

The lactogenic formulations of this invention promote growth of a number of *Lactobacillus* probiotics including *Lactobacillus acidophilus* LA-1, *Lactobacillus paracasei* F-19 and *Lactobacillus rhamnosus* HN001 and Lr-32, as exemplified herein, and may also be used with other *Lactobacillus* probiotic species, including: *L. casei, L. bulgaricus, L. fermentum, L. plantarum, L. delbrukeii, L. salivarius, L. jensenii, L. gaserii, L. reuteri, L. helveticus, L. lactis, L. brevis*, and *L. johnsonii*. The mode of action may be due to the generation of monoaccharides and free amino acids and/or short chain peptides at or near the intestinal colonization sites of the *lactobacilli* (which are predominantly in the small intestine). These same monosaccharides and amino acids stimulate bifidobacteria in vitro but, in practice, due to their rapid absorption and utilization in the small intestine, rarely make it to the colon where the bifidobacteria reside. Therefore, one preferred embodiment of the lactogenic formulations includes one or more protease enzymes as well as carbohydrase enzymes, e.g., alpha-amylase and glucoamylase. Each enzyme is supplied at the minimum activity specified in Table 1. Another embodiment includes the aforementioned enzymes plus the additional carbohydrase enzymes, lactase and invertase, that split the disaccharides lactose and sucrose, respectively, releasing the monosaccharides glucose, galactose and fructose. The diet of the person or animal being treated dictates which embodiments to utilize; for example, a diet lacking lactose would not require inclusion of lactase.
Bifidogenic Enzyme Formulations (BEF)

The bifidogenic formulations herein promote growth of *Bifidobacterium* probiotics such as *Bifidobacterium lactis* HN019, BL-04 and *Bifidobacterium bifidum* BB-12 as exemplified herein, but can also be used to promote growth of other *Bifidobacterium* probiotic species, e.g., *B. animalis, B. breve, B. longum*, and *B. infantis*. The mode of action may involve two separate actions: 1) The release of performed prebiotics (such as fructooligosaccharides or FOS) present in fruits, vegetables and whole grains, that are otherwise trapped in a cellulose matrix that makes them less bioavailable; and 2) The enzymatic cracking of hemicellulose and other non-cellulose polysaccharides into oligosaccharides that have prebiotic activity. Therefore, one embodiment of the bifidogenic formulations includes at least one cellulase enzyme and hemicellulase in amounts (activity units) specified in Table 1, where the cellulase releases existing prebiotics while the hemicellulase cracks non-cellulose polysaccharides, both of which are bifidogenic effects. Another embodiment includes addition of pectinase and beta-glucanase, in amounts shown in Table 1, to this formulation. Again, the diet is controlling, in that diets rich in pectins and beta-glucans would benefit from the inclusion of pectinase and beta-glucanase.

Exemplary fiber-digesting enzymes in the bifidogenic enzyme formulation include the following: cellulase-TL from *Trichoderma longibrachiatum* (150,000 CU/g), cellulase-AN from *Aspergillus niger* (50,000 CU/g), beta-glucanase from *T. longibrachiatum* (3,000 BGU/g), hemicellulase from *A. niger* (400,000 HCU/g), pectinase from *A. niger* (500,000 AJDU/g), and xylanase from *T. longibrachiatum* (150,000 XU/g). Activity units in parenthesis are those of the stock enzyme concentrates, purchased commercially, and are not necessarily the activities in the final formulations. All enzymes are dry powders available from Bio-Cat, Inc., Troy, Va.

Standardization, mixing and packaging for BEF formulations are essentially the same as noted above for LEF. Lactogenic and bifidogenic formulations generally will both be included in the final formulation since most commercial probiotic formulations contain both *Lactobacillus* and bifidobacteria.

Polysorbate Formulations

The polysorbate formulations of this invention contain food grade polysorbate surfactants: Polysorbate-60, polysorbate-80 or any polysorbate with an HLB>12, where HLB is the hydrophile-lipophile balance, designated from 1 to 20. Surfactants having HLB values greater than 12 are more hydrophilic than lipophilic and produce oil in water emulsions. The chemical name for Polysorbate 60 is polyoxyethylene sorbitan monostearate, having an HLB of 14.9. polysorbate-80 is polyoxyethylene sorbitan monooleate, having an HLB of 15.0. A source for suitable polysorbates are the Tweens, specifically Tween-60 and Tween-80, available from ICI Specialties, Wilmington, Del.

Polysorbates are oily, sticky, non-aqueous liquids that are not compatible with dry enzymes. Mixing them directly with dry enzymes destabilizes the enzymes resulting in shortened shelf life as exemplified herein. Therefore, dry polysorbate products that will result in shelf stable formulations when mixed with dry enzymes are preferred. Polysorbates such as Tween-60 or Tween-80, are not available commercially in dry form and it is not possible to dry liquid polysorbates by heating them, as heat causes decomposition. It has been discovered that polysorbates can be dried by absorbing them into powdered silicates, e.g., alumnosilicates, silicas, food starches, or combinations thereof, which involves mixing a liquid polysorbate directly into the powdered material.

Drying Polysorbates

Although a variety of absorbent substances such as clays, starches, and hydrocolloid gums can be used to produce dry-absorbed polysorbate products suitable for formulations herein, one formulation is advantageous, as it results in a dry powder with a polysorbate concentration of 35% or more. That formulation is made as follows: Polysorbate in the form of Tween-80 or Tween-60 is slowly poured into calcium silicate (Hubersorb-600 from J.M. Huber Corp., Harve de Grace, Md.) that is under constant agitation in a Hobert type, double-action, rotary mixer. Seventy (70) grams of polysorbate is added per 30 grams of Hubersorb-600 over a period of 30 minutes while mixing at 100 RPM; resulting in a mixture that is dry but somewhat lumpy. To each 100 grams of this Polysorbate-Hubersorb mixture 20 grams of silica (Syloid 63 FP, W.R. Grace, Columbia, Md.) and 80 grams of potato starch (Perfectamyl D6, Avebe) are slowly added with constant mixing, typically done in the same mixer, and requiring about 30 minutes at 100 RPM. The final formulation contains per 100 grams: 35 grams Tween-80, 40 grams potato starch, 15 grams Hubersorb-600 and 10 grams silica. The potato starch is dried under an infrared lamp prior to use for 7 hours at 220 F to remove approximately 14% of the moisture.

The resulting dry powder has a polysorbate concentration of 35% and a water activity of less than 0.04 and is referred to herein as DP35 (Dry Polysorbate 35%). DP35 and can be blended with the enzyme formulations of the present invention without adversely affecting shelf life at room temperature (65-85 F), or can be administered separately, in capsules for example, in a kit containing the enzyme and probiotic formulations.

The concentration of polysorbate required to effect an enhancement of enzyme activity that concomitantly results in an enhancement of probiotic colonization or IPC ranges from 0.02 to 0.2% of the weight of the food matrix (food or test diet) being consumed, and is equivalent to 0.057 to 0.57% DP35. The DP35 is either mixed with the enzyme formulations at 10-80% by weight, or is supplied separately.

The advantages that polysorbates confer can be realized by orally ingesting liquid polysorbates; for example, by adding polysorbates to fruit juice or some similar beverage, or by encapsulating the polysorbates in sealed pharmaceutical grade capsules suitable for liquids. However, when administered separately, they may cause digestive upset or an unpleasant after taste.

Enzyme Strength in LEF and BEF Formulations

Each enzyme must have a certain minimum activity, measured as activity units per administered dose, in order to achieve significant probiotic enhancement. This holds true whether the enzymes are administered individually or in combination with other enzymes, however, the activities can be additive. Thus, when compounding enzyme mixtures, for example, a lactogenic enzyme formulation containing three protease enzymes all at the minimum recommended activity per dose (see Table 1) will generate more protein digestion than any one of the proteases used alone at its recommended minimum activity. Thus, formulations can be developed utilizing in vitro probiotic models, where a given formulation can be designed to fit a desired dose program. For example, a formulation containing three protease enzymes may not need to be administered as frequently as one containing only one protease. In addition, there are other situations where a particular combination of enzymes is required to maximize probiotic enhancement; for example, to release monosaccharides from starch, a combination of alpha-amylase and glucoamylase is preferred. In this case, the minimum activity is specified for glucoamylase in Table 1. Although it will release monosaccharides to some extent when administered alone, since pancreatic alpha-amylase is present in the intestinal tract, it is more effective when administered in combination with alpha-amylase.

Table 1 discloses the minimum activity required for each enzyme per formulation dose, where, one dose is the amount of formulation ingested in one oral administration. The frequency of oral administrations (doses) can range from one to four times daily, to once daily, to less frequently such as once every-other-day or once or twice weekly, or otherwise. When more than one enzyme is present in a LEF, BEF or a joint formulation, each enzyme should meet or exceed the minimum activity per dose indicated in Table 1. The activity units specified in Table 1 are those used by the commercial suppliers for these enzymes; however, there are different activity units and different assay procedures which can be used to measure the activity. The assay used often depends on the intended application and/or the manufacturer of the enzymes. However, equivalent biological activity can be determined by laboratory analysis. Venture Laboratories, Inc. in Lexington, Ky., provides enzyme analysis by different methods.

TABLE 1

Enzyme (Minimum Activity Required/Dose)

Papain (10,000 TU = Tyrosine Units)
Bromelain (50 GDU = Gelatin Dissolving Units)
Fungal Protease (1,000 HU = Hemoglobin Units)
Acid Protease (50 SAP)
Fungal Peptidase (10 LAP)
Alpha-Amylase (1,000 SKB = Sandstedt, Kneen and Blish Units)
Glucoamylase (2.5 AG = Amyloglucosidase Units)
Lactase (100 ALU = Acid Lactase Units)
Invertase (100 SU = Sumner Units)
Cellulase-TL (1,000 CU = Cellulase Units)
Cellulase-AN (500 CU = Cellulase Units)
Hemicellulase (1,000 HCU = Hemicellulase Units)
Pectinase (1,000 AJDU = Apple Juice Depectinizing Units)
Beta-Glucanase (50 BGU = Beta-Glucanase Units)
Xylanase (1,000 XU = Xylanase Units)

Probiotic Formulations

The probiotic formulations containing *Lactobacillus* or *Bifidobacterium* species or a combination thereof, have total viable plate counts within the range of 500 million to 1 trillion CFU/g (colony forming units/gram). A minimum viable plate count per dose is about 5 billion CFUs. Viable plate counts are determined by procedures outlined in Standard Methods for the Examination of Dairy Products (16th ed.) using a modified De Man Rogosa and Sharpe agar (MRS) to which L-cysteine HCL is added. The counts are reported in colony forming units, either per gram or per dose.

Exemplary *Lactobacillus* species suitable for the formulations herein include: *L. casei, L. bulgaricus, L. fermentum, L. plantarum, L. delbrukeii, L. salivarius, L. jensenii, L. gaserii, L. reuteri, L. helveticus, L. lactis, L. brevis, L. johnsonii, L. acidophilus, L. paracasei*, and *L. rhamnosus*.

Exemplary *Bifidobacterium* species include; *B. animalis, B. breve, B. longum, B. infantis, B. lactis* and *B. bifidum*.

Formulations are generally compounded from freeze-dried concentrates of probiotic species from commercial sources, where the strain designations for each are indicated. The following strains are suitable for use: *Lactobacillus acidophilus* LA-1, *Lactobacillus rhamnosus* HN001, *Lactobacillus rhamnosus* Lr-32, *Lactobacillus casei* 163, *Bifidobacterium lactis* HN019 and *Bifidobacterium lactis* BL-04 from Danisco USA, Inc. Madison, Wis. *Bifidobacterium bifidum* BB-12 from Chr. Hansen, West Allis, Wis. and *Lactobacillus paracasei* F-19 from Medipharm USA, Des Moines, Iowa). The probiotics are blended with microcrystalline cellulose (Avicel PH 112, FMC) and silica (Syloid 63 FP, W.R. Grace) to achieve the desired CFU/g. The amount of silica generally should not exceed 2% by weight. Blending is preferably carried out under dry conditions (relative humidity about 20%) in a Patterson Kelly type, twin-cone mixer until a uniform mixture is obtained (usually requires 10-15 minutes at 100 RPM). The water activity of the blend should be below Aw=0.03 for optimum shelf life. Magnesium stearate, pharmaceutical grade, is added at 2% by weight to formulations which are intended for filling into hard capsules or tableting.

Water activity (Aw) is equivalent to the relative humidity generated in a closed container containing the sample multiplied by 0.01, or 1.0% relative humidity=0.01 Aw. Measurement of Aw in the examples herein was conducted using a Rotronic Hygrometer Model A2 from Rotronic Instrument Corp., Huntington. N.Y.

The following examples will further illustrate the present invention but are not intended to limit the scope of the invention.

Example No. 1

I) *Lactobacillus acidophilus* LA-1 was inoculated at one (1) million CFU/ml into 500 ml of sterile broth medium containing 2% casein, 2% corn starch, 0.1% calcium carbonate, 0.1% magnesium carbonate, and 0.05% yeast extract (Difco); a medium in which it is difficult to achieve significant *Lactobacillus* growth but which contains typical nutrients found in human diets. The inoculated broth (contained in 1 L Erlenmeyer flasks) was incubated at 37 C for 24 hours and then plated on MRS agar to determine CFU/ml. Result (average of triplicate samples): 12 million CFU/ml.

II) The test in (I) was repeated where the medium also contained 0.1% Tween-80. Result: 14 million CFU/ml.

III) The test in (I) was repeated where the medium was pre-treated with digestive enzymes for 24 hours prior to sterilization at 121 C for 20 minutes at 15 psi. The pre-treatment involved adding 250 mg of a lactogenic enzyme mixture containing papain (10,000 TU), bromelain (50 GDU), alpha-amylase (1,000 SKB) and glucoamylase (2.5 AG).
Result; 87 million CFU/ml.

IV) The test in (III) was repeated where 0.1% Tween-80 (as DP35) was added during the enzyme pre-treatment procedure. Result: 128 million CFU/ml.

Conclusion: Lactogenic enzyme pre-treatment significantly stimulates the growth of *L. acidophilus* LA-1 and enzyme pre-treatment plus Tween-80 yields even significantly stimulation.

Example No. 2

The procedures of Example 1 were repeated with *Lactobacillus rhamnosus* HN001 substituted for *Lactobacillus acidophilus* LA-1. The results are as follows: Test I): 6 million CFU/ml. Test II): 7.5 million CFU/ml. Test III): 62 million CFU/ml. Test IV): 106 million CFU/ml.

Conclusion: Lactogenic enzyme pre-treatment significantly stimulates the growth of *L. rhamnosus* HN001 and enzyme pre-treatment plus Tween-80 yields significantly greater stimulation.

Example No. 3

The procedures of Example 1 were repeated with *Lactobacillus paracasei* F-19 substituted for *Lactobacillus acidophilus* LA-1. The results are as follows: Test I): 14 million CFU/ml. Test II): 19 million CFU/ml. Test III): 88 million CFU/ml. Test IV): 148 million CFU/ml.

Conclusion: Lactogenic enzyme pre-treatment significantly stimulates the growth of *L. paracasei* F-19 and enzyme pre-treatment plus Tween-80 yields significantly greater stimulation.

Example No. 4

V) The procedures of Example 1 were repeated with *Lactobacillus acidophilus* LA-1 except that the enzyme pre-treatment step was as follows: The pre-treatment involved adding 250 mg of a lactogenic enzyme mixture containing fungal protease (1,500 HU), acid-protease (50 SAP), fungal peptidase (10 LAP), alpha-amylase (1,000 SKB) and glucoamylase (2.5 AG). In addition, Tween-60 was used in place of Tween-80. The results are as follows: Test I): 10 million CFU/ml. Test II): 9 million CFU/ml. Test III): 74 million CFU/ml. Test IV): 108 million CFU/ml.

Conclusion: This different lactogenic enzyme pre-treatment also significantly stimulates the growth of *L. acidophilus* LA-1 and enzyme pre-treatment plus Tween-60 yields significantly greater stimulation.

Example No. 5

I) *Bifidobacterium lactis* BL04 was inoculated at two (2) million CFU/ml into 500 ml of sterile broth medium containing 2% casein, 1% rye flour, 1% asparagus powder (ground freeze-dried asparagus), 1% barley flour, 0.1% calcium carbonate, 0.1% magnesium carbonate, and 0.05% yeast extract (Difco); a medium in which it is generally difficult to achieve significant Bifidobacteria growth but contains typical nutrients found in human diets. The inoculated broth (contained in 1 L Erlenmeyer flasks) was incubated anaerobically at 37 C for 24 hours and then plated on MRS agar plus L-cysteine HCL to determine CFU/ml (plates were incubated anaerobically). Result (average of triplicate samples): 8 million CFU/ml.

II) The test in I) was repeated where the medium also contained 0.025% Tween-80. Result: 3 million CFU/ml.

III) The test in I) was repeated where the medium was pre-treated with digestive enzymes for 24 hours prior to sterilization at 121 C for 20 minutes at 15 psi. The pre-treatment involved adding 250 mg of a bifidogenic enzyme mixture containing cellulase-TL (1,000 CU), hemicellulase (1,000 HCU), beta-glucanase (50 BGU), papain (10,000 TU) and bromelain (50 GDU). Result: 74 million CFU/ml.

IV) The test in III) was repeated where 0.025% Tween-80 was added during the enzyme pre-treatment procedure. Result: 98 million CFU/ml.

Conclusion: Bifidogenic enzyme pre-treatment of a medium containing largely prebiotic carbohydrate substances significantly stimulates the growth of *Bifidobacterium lactis* BL04, and enzyme pre-treatment plus Tween-80 yields significantly greater stimulation i.

Example No. 6

The procedures of Example #4 were repeated with *Bifidobacterium bifidum* BB-12 substituted for *Lactobacillus acidophilus* LA-1. The results are as follows: Test I): 11 million CFU/ml. Test II): 5 million CFU/ml. Test III): 88 million CFU/ml. Test IV): 104 million CFU/ml.

Conclusion: Bifidogenic enzyme pre-treatment of a medium containing largely prebiotic carbohydrate substances significantly stimulates the growth of *Bifidobacterium bifidum* BB-12 and enzyme pre-treatment plus Tween-80 yields significantly greater stimulation i.

Example No. 7

I) 10 grams of papain was blended with 88 grams of microcrystalline cellulose (Avicel PH112) and 2 grams of silica (Syloid 63 FP) in a mortar with gentle mixing to achieve an activity of 80,000 TU/g and a water activity of 0.04. After storage at 25 C for 6 months in a sealed glass bottle the resulting activity was 75,200 TU (6% loss).

II) 10 grams of papain was blended with 78 grams of Avicell PH112, 2 grams of Syloid 63 FP and 10 grams of liquid Tween-80 (100% polysorbate) in a mortar with gentle mixing to achieve an activity of 80,000 TU/g and a water activity of 0.25. After storage at 25 C for 6 months in a sealed glass bottle the resulting activity was 68,800 TU (14% loss).

III) 10 grams of papain was blended with 59.4 grams of Avicel PH112, 2 grams of Syloid 63 FP and 28.6 grams of dry Tween-80 containing 35% polysorbate (DP35), produced according to the method disclosed in this invention, to achieve an activity of 80,000 TU/g and a water activity of 0.05. After storage at 25 C for 6 months in a sealed glass bottle the resulting activity was 75,000 TU (6.25% loss).

Conclusion: Liquid Tween-80 containing 100% polysorbate cannot be blended with papain without causing a significant reduction in product shelf life. DP35 produced by the method, disclosed herein can be blended with papain without any significant difference in shelf life compared to a papain mixture without Tween-80.

Example No. 8

The process of Example 7 was repeated with lactase instead of papain: 10 grams of lactase blended into formulation I) resulted in an initial activity of 10,000 ALU/g. The shelf life results are: Lactase without Tween-80 after 6 mo. storage tested 9,200 ALU (8% loss); lactase with liquid Tween-80 tested 6,200 ALU (38% loss); lactase with DP35 tested 9,000 ALU (10% loss).

Conclusion; Liquid Tween-80 containing 100% polysorbate cannot be blended with lactase without causing a significant reduction in shelf life. DP35 produced by the method disclosed herein can be blended with lactase without a significant difference in shelf life compared to the mixture without Tween-80.

Example No. 9

The process of Example 7 was repeated with hemicellulase instead of papain; 10 grams of hemicellulase blended into formulation I) resulted in an initial activity of 40,000 HCU/g. The shelf life results are; Hemicellulase without Tween-80 after 6 mo. storage tested 39,000 (2.5% loss); hemicellulase with liquid Tween-80 tested 32,000 (20% loss); hemicellulase with DP35 tested 38,800 HCU (3.0% loss).

Conclusion; Liquid Tween-80 containing 100% polysorbate cannot be blended with hemicellulase without causing a significant reduction in shelf life. DP35 produced by the method disclosed herein can be blended with hemicellulase without a significant difference in shelf life compared to the mixture without Tween-80.

Example No. 10

Reference is made to the following scientific publication: Effect of Feeding Lactobacilli on the Coliform and *Lactobacillus* Flora of Intestinal Tissue and Feces from Piglets by K. S. Muralidhara, G. G. Sheggeby, P. R. Elliker, D. C. England, and W. E. Sandine in: Journal of Food Protection, Volume 40, Number 5, Pages 288-295, May, 1977. This example will use certain procedures of that publication, with exceptions noted, to demonstrate the in vivo effectiveness of the formulations discussed herein.

The probiotic formulation used had the following composition per 445 mg (net weight) HPMC capsule:

*Lactobacillus acidophilus* LA-1, 5 billion CFU; *Lactobacillus paracasei* F-19, 5 billion CFU; *Lactobacillus rhamnosus* HN001, 2 billion CFU; one billion CFU=1,000,000,000. These probiotics were in a blend containing the following excipients: Avicel PH112, Syloid 63 FP and magnesium stearate as outlined under the heading "Probiotic Formulations," and the resulting formulation had a water activity of 0.03.

The enzyme formulation had the following composition per 460 mg (net weight) HPMC capsule: Alpha amylase 5,000 SKB, glucoamylase 5 AG, bromelain 150 GDU, papain 42,500 TU, neutral protease 5,800 HU, DP35 (35% dry Tween-80) 160 mg.

Twelve weaned piglets from central Iowa, approximately 4 weeks old weighing an average of 7 kg each were assigned to individual pens, one pig per pen, and fed the following basal diet ad lib (all ingredients listed as weight %): Yellow corn 42%, soybean meal 24%, ground oats 10%, dehydrated alfalfa meal 5%, brewers dried yeast 1%, dicalcium phosphate 1.1%, ground limestone 1.15%, fish solubles 2%, lard 2.5%, dried whey 10%, vitamin/trace mineral premix 1.25%. Drinking water was also provided ad lib. Four pigs were designated controls and received only the basal ration, four received additionally the probiotic formula at 2 capsules daily in the morning, and four received the probiotic formula at 2 capsules daily in morning and the enzyme formula at 2 capsules daily in the afternoon, about 7 hours later. Microbiological analyses were performed in triplicate on fresh fecal samples, on location: *Lactobacillus* counts were determined on MRS agar (BBL Labs) containing L-cysteine HCl and coliform counts were determined on MacConkey's agar (Difco), all were incubated at 37 C for 48 hours. Plate counts were made at the end of 4 weeks and are reported here as averages of triplicate determinations in CFU/gram. One pig in the control group scoured and was removed form the study. Results: Control pigs, coliforms=840,000,000 CFU, lactobacilli=320,000,000 CFU. Pigs fed probiotic formula, coliforms=22,000,000 CFU, lactobacilli=615,000,000 CFU. Pigs fed probiotic and enzyme formulas: coliforms=790,000 CFU, lactobacilli=989,000,000 CFU.

Conclusion: Pigs fed the probiotic formula had higher fecal *lactobacillus* counts and lower coliform counts versus control pigs, and pigs fed both the probiotic formula and the enzyme formula had the highest fecal *lactobacillus* counts and lowest coliform counts.

Example No. 11

A similar feeding trial to Example 10 was ran with the following exceptions:
The probiotic formulation used had the following composition per 445 mg (net weight) HPMC capsule;
*Lactobacillus acidophilus* LA-1, 5 billion CFU; *Lactobacillus paracasei* F-19, 5 billion CFU; *Lactobacillus rhamnosus* Lr-32, 2 billion CFU; *Bifidobacterium lactis* BL04, 5 billion CFU;
*Bifidobacterium bifidum* BB-12, 3 billion CFU. The probiotics were in a blend containing the following excipient: Avicel PH112, Syloid 63 FP and magnesium stearate as outlined under Probiotic Formulations, the resulting formulation had a water activity of 0.028.

The enzyme formulation had the following composition per 460 mg (net weight) HPMC capsule: Alpha amylase 5,000 SKB, glucoamylase 5 AG, bromelain 150 GDU, papain 42,500 TU, neutral protease 5,800 HU, cellulase-TL 3,000 CU, hemicellulase 6,400 HCU, pectinase 7,500 ADJU, DP35 (35% dry Tween-80) 120 mg.

Twelve weaned piglets from central Iowa, approximately 4 weeks old weighing an average of 6.5 kg each were assigned to individual pens, one pig per pen, and fed the following basal diet ad lib (all ingredients listed as weight %): Yellow corn 42%, soybean meal 24%, ground oats 10%, dehydrated alfalfa meal 5%, brewers dried yeast 1%, dicalcium phosphate 1.1%, ground limestone 1.15%, fish solubles 2%, lard 2.5%, dried whey 10%, vitamin/trace mineral premix 1.25%. Drinking water was also provided ad lib. Four pigs were designated controls and received only the basal ration, four received additionally the probiotic formula at 2 capsules daily in the am, four received the probiotic formula at 2 capsules daily in morning and the enzyme formula at 2 capsules daily in the afternoon about 6 hours later. Microbiological analyses were performed in triplicate on fresh fecal samples, on location: *Lactobacillus*/Bifidobacteria counts were determined on MRS agar (BBL Labs) containing L-cysteine HCl and coliform counts were determined on MacConkey's agar (Difco), all were incubated at 37 C for 48 hours, and the MRS plates were incubated in an anaerobic jar. Plate counts were made at 4 weeks and are reported here as averages at the end of the forth week in CFU/gram (averages of triplicate plate counts).

Results: Control pigs, coliforms=970,000,000 CFU, lactobacilli=262,000,000 CFU. Pigs fed probiotic formula, coliforms=740,000,000 CFU, lactobacilli+bifidobacteria=876,000,000 CFU. Pigs fed probiotic and enzyme formulas: coliforms=160,000 CFU, lactobacilli+bifidobacteria=1,428,000,000 CFU.

Conclusion: Pigs fed the probiotic formula had higher fecal *lactobacillus*+bifidobacteria counts and lower coliform counts versus control pigs, and pigs fed both the probiotic formula and the enzyme formula had the highest fecal *lactobacillus* and bifidobacteria counts and the lowest coliform counts.

Example No. 12

The probiotic and enzyme formulations of Example 11 were fed to two caucasian males in good health, each 25 years old, living in Los Angeles, Calif. Both consumed a typical western diet averaging 2000 calories per day. Dinners contained one serving each of a green and yellow vegetable plus meat and a starch based food such as potatoes, pasta or rice. Phase 1: The probiotic formulation was taken daily, 2 capsules with water before breakfast at 9:00 am, for two weeks. Microbiological analyses of stool samples (MRS and MacConkey agar platings as in Example 11) were determined at the end of the two week period. Phase 2: Subsequently, a second two week period was initiated where the probiotic formulation was continued as in phase 1 but was followed by two capsules of the enzyme formulation, daily, at dinner at 5:00 PM. Two weeks later the microbiological analyses were repeated.

Results Individual A: Phase 1 coliforms=66,000,000 CFU/g, lactobacilli+bifidobacteria=541,000,000 CFU. Phase 2 coliforms=440,000, lactobacilli+bifidobacteria=1,898,000,000 CFU/g.

Results Individual B: Phase 1 coliforms=198,000,000 CFU/g, lactobacilli+bifidobacteria=888,000,000 CFU. Phase 2 coliforms=676,000, *lactobacilli*+bifidobacteria=2,247,000,000 CFU/g.

Conclusion; A dramatic, response to probiotics plus enzymes-polysorbate treatment was demonstrated, i.e., coliform counts were significantly lower and probiotic counts significantly higher compared to probiotic treatment alone.

Example No. 13

The probiotic and enzyme formulations of Example 11 were fed to two caucasian females in good health, each 42 years old, living in Los Angeles, Calif. Both consumed a typical western diet averaging 2000 calories per day. Dinners contained one serving each of a green and yellow vegetable plus meat and a starch based food such as potatoes, pasta or rice.

Phase 1: The probiotic formulation was taken every-other-day, 2 capsules with water before breakfast at 9:00 am, for two weeks. Microbiological analyses of stool samples (MRS and MacConkey agar platings as in Example 11) were determined at the end of the two week period. Phase 2: Subsequently, a second two week period was initiated where the probiotic formulation was continued as in phase 1 but was followed by three capsules of the enzyme formulation twice weekly (3 days apart) at dinner at 5:00 PM. Two weeks later the microbiological analyses were repeated.

Results Individual C: Phase 1 coliforms=336,000,000 CFU/g, lactobacilli+bifidobacteria=589,000,000 CFU. Phase 2 coliforms=104,000,000 lactobacilli+bifidobacteria=1,016,000,000 CFU/g.

Results Individual D: Phase 1 coliforms=88,000,000 CFU/g, lactobacilli+bifidobacteria=741,000,000 CFU. Phase 2 coliforms=38,000,000 lactobacilli+bifidobacteria=989,000,000 CFU/g.

Conclusion: A marked response of probiotics plus enzyme-polysorbate treatment was demonstrated at this dosage frequency as well, i.e., fecal coliform counts were lower and probiotic counts higher than with probiotics alone. But the response was not as marked as with daily dosing of probiotics and enzymes plus polysorbate as in Example 12.

It must be understood that this invention is not limited to the particular compositions, process steps, administration programs and materials disclosed herein, in the description or examples, but that these may vary.

The scope of the invention is not defined or limited by the examples or the terms or expressions herein, but is defined only in the claims that follow, and includes all equivalents of the subject matter of the claims.

What is claimed is:

1. A formulation that promotes in vivo colonization of probiotic microorganisms in humans or animals comprising digestive protease enzymes, digestive carbohydrases and fiber-digesting enzymes, *Lactobacillus* and *Bifidobacterium* probiotic bacteria, and a dry polysorbate, of which said dry polysorbate is prepared by mixing TWEEN-80 first with calcium silicate and then with silica and starch and wherein the dry polysorbate contains per 100 grams of the dry polysorbate: about 35 grams of TWEEN-80, about 40 grams of starch, about 15 grams of calcium silicate and about 10 grams of silica, and wherein the Aw of the formulation is below 0.04.

2. The formulation of claim 1 wherein the *Lactobacillus* probiotic species is *Lactobacillus acidophilus, Lactobacillus rhamnosus, Lactobacillus casei, Lactobacillus paracasei, Lactobacillus bulgaricus, Lactobacillus fermentum, Lactobacillus plantarum, Lactobacillus delbrukeii, Lactobacillus salivarius, Lactobacillus jensenii, Lactobacillus gaserii, Lactobacillus reuteri, Lactobacillus helveticus, Lactobacillus lactis, Lactobacillus brevis, Lactobacillus johnsonii, Lactobacillus acidophilus* LA-1, *Lactobacillus rhamnosus* HN001, *Lactobacillus rhamnosus* Lr-32, *Lactobacillus casei* 163, *Lactobacillus paracasei* F-19 or any mixture thereof.

3. The formulation of claim 1 wherein the *Bifidobacterium* probiotic species is *Bifidobacterium lactis, Bifidobacterium animalis, Bifidobacterium longum, Bifidobacterium bifidum, Bifidobacterium breve, Bifidobacterium infantis, Bifidobacterium lactis* HN019, *Bifidobacterium lactis* BL-04, *Bifidobacterium bifidum* BB-12, or any mixture thereof.

4. The formulation of claim 1 wherein the probiotic bacteria are blended with microcrystalline cellulose and silica.

5. The formulation of claim 1 further including alumnosilicates.

6. The formulation of claim 4 wherein the amount of silica does not exceed 2% by weight.

7. The formulation of claim 1 wherein: the protease enzymes are papain, bromelain, fungal protease, fungal acidprotease, bacterial protease, fungal peptidase, nattokinase, serapeptase, trypsin, chymotrypsin pancreatin and pepsin.

8. The formulation of claim 1 wherein the carbohydrase enzymes are alpha-amylase, amylase, glucoamylase, lactase, and invertase, and the fiber-digesting enzymes are, cellulase-TL, cellulase-AN, hemicellulase, pectinase, beta-glucanase, and xylanase.

9. The formulation of claim 1 where the enzymes comprise 10-80% of the formulation.

10. The formulation of claim 7 where the enzymes are present at the following minimum activity units per dose: Papain at 10,000 TU, bromelain at 50 GDU, and fungal peptidase at 10 LAP.

11. The formulation of claim 8 wherein the enzymes are present at the following minimum activity units per dose: the alpha-amylase at 1,000 SKB, glucoamylase at 2.5 AG, lactase at 100 ALU, invertase at 100 SU, cellulase at 1,000 CU, cellulase-TL at 1,000 CU, cellulase-AN at 500 CU, hemicellulase at 1,000 HCU, pectinase at 1,000 AJDU, beta-glucanase at 50 BGU, and xylanase at 1,000 XU.

12. The formulation of claim 1 wherein the formulation is in the form of a capsule, tablet, or packet.

* * * * *